(12) United States Patent
Zeng (10) Patent No.: US 9,867,672 B2
(45) Date of Patent: Jan. 16, 2018

(54) GLOVE WITH A CUFF (71) Applicant: CORE PACIFIC, LLC, Houston, TX (US)

(72) Inventor: Qing Hai Zeng, Houston, TX (US)

(73) Assignee: Core Pacific, LLC, Houston, TX (US)

(*) Notice: Subject to any disclaimer, the term of this patent is extended or adjusted under 35 U.S.C. 154(b) by 386 days.

(21) Appl. No.: 14/599,471

(22) Filed: Jan. 17, 2015

(65) Prior Publication Data
US 2015/0282540 A1 Oct. 8, 2015

Related U.S. Application Data (60) Provisional application No. 61/975,834, filed on Apr. 6, 2014.

(51) Int. Cl.
*A41D 19/00* (2006.01)
*A61B 42/00* (2016.01)
*A61B 42/50* (2016.01)

(52) U.S. Cl.
CPC .......... *A61B 42/00* (2016.02); *A41D 19/0048* (2013.01); *A41D 19/0089* (2013.01); *A61B 42/50* (2016.02)

(58) Field of Classification Search
CPC ........ A61B 19/04; A61B 42/50; A41D 19/015
USPC .............................. 2/168, 161.7, 161.6, 161.1
See application file for complete search history.

(56) References Cited

U.S. PATENT DOCUMENTS

| | | | | |
|---|---|---|---|---|
| 2,106,348 A | * | 1/1938 | Hall | A41D 19/0055 2/168 |
| 3,099,015 A | * | 7/1963 | Renehan | A41D 19/0089 285/260 |
| 4,756,027 A | * | 7/1988 | Buenos | A41D 19/0041 2/123 |
| 5,953,756 A | | 9/1999 | Vrissimdjis et al. | |
| 6,249,917 B1 | | 6/2001 | Vrissimdjis et al. | |
| 7,480,945 B2 | | 1/2009 | Knuth et al. | |
| 7,624,455 B1 | * | 12/2009 | Bhalla | A41D 19/0055 2/160 |
| 7,832,019 B1 | * | 11/2010 | Bhalla | A41D 19/0044 2/160 |
| 8,146,174 B2 | | 4/2012 | Knuth et al. | |
| 2013/0298308 A1 | * | 11/2013 | George | A41D 19/015 2/161.7 |

* cited by examiner

*Primary Examiner* — Tejash Patel
(74) *Attorney, Agent, or Firm* — Andrew W. Chu; Craft Chu PLLC (57) ABSTRACT

The glove includes a hand portion, a sleeve portion integral to the hand portion and extending conically outward, a cuff portion integral with the sleeve portion and extending conically outward, and a connection portion between the cuff portion and the sleeve portion. The cuff portion folds over the sleeve portion at the connection portion. The connection portion includes at least one annular ridge with a respective surface, a first V-shaped channel on a first side of the surface, and a second V-shaped channel on a second side of the surface. The V-shaped channels form creases or bottom portions with a thickness smaller than either the sleeve portion, rim portion, or cuff portion. The V-shaped channel preset a pivot for folding the cuff portion over the sleeve portion.

20 Claims, 3 Drawing Sheets

GLOVE WITH A CUFF

RELATED U.S. APPLICATIONS

The present application claims priority under 35 U.S.C. Section 119(e) from U.S. Provisional Patent Application Ser. No. 61/975,834, filed on Apr. 6, 2014, entitled "GLOVE WITH A CUFF".

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to a glove. More particularly, the present invention relates to rubber or latex glove with a cuff. Even more particularly, the present invention relates to a rubber glove with preset pivot to fold over a locked cuff.

2. Description of Related Art Including Information Disclosed Under 37 CFR 1.97 and 37 CFR 1.98.

Rubber gloves are commonly used for washing dishes and other household chores to protect the wearer from chemicals in cleaning products. The gloves also protect the wearer from water and wetness, which can damage skin and be uncomfortable. The protective rubber gloves can also insulate from the temperature of the water and prevent exposure to bacteria and germs in the water. There are also medical and foodservice applications of rubber gloves. Typically, latex is the type of rubber used to form the gloves, although other materials, such as PVC and neoprene, can be used.

The technology of gloves has developed. The aesthetic appearance of the glove can be modified in color and pattern. The thickness and weight of the rubber can also change. Particular elements are also added to gloves to affect functionality. The hand portion of the glove can be textured for improved grip. A liner can be inserted to prevent allergic reaction to latex. A cuff can be added to seal against the arm of the wearer. The cuff can have structure and texture for comfort and for preventing liquid from dripping into the glove.

Various patents have been granted in the field of glove with a cuff. U.S. Pat. No. 8,146,174, issued on Apr. 3, 2012 to Knuth et al, discloses a glove with an obstruction on the arm covering portion to trap liquid and prevent contact with the wearer. There are three segments with a fold over to form the cuff. U.S. Pat. No. 7,480,945, issued on Jan. 27, 2009 also to Knuth et al, discloses a glove with another version of an obstruction on the arm covering portion. A U-shaped indentation separates a flared end to fold over the indentation. U.S. Pat. No. 6,249,917, issued on Jun. 26, 2001 to Vrissimdjis et al, teaches another glove with a cuff. A thinned wall portion between the hand covering portion and the arm covering portion has a smaller thickness so that the end of the arm covering portion folds over to form the cuff. Annular beads can hold the fold, maintaining structure of the cuff. U.S. Pat. No. 5,953,756, issued on Sep. 21, 1999 also to Vrissimdjis et al, describes another cuff on a glove formed by an undulation and a thickened wall portion.

The prior art systems of gloves with a cuff are difficult and expensive to manufacture. Creating the beads, bulges and undulations require specialized machining and extra steps by nature of latex construction. Pouring latex over a mold does not easily create cuffing structures of the prior art systems. In the patents by Vrissimdjis, the annular beads and thickened wall portions require an extra step of setting an annular ring to cause the latex to pool at the specific location (the '756 patent). There must also be a wall portion to weaken the structure of the glove. The wall portion allows the fold at the structurally weaker portion of the glove. There could also be an extra step of dipping another layer of latex to coat the annular bead (the '917 patent). Similarly, the patents by Knuth rely on the same theory of construction of latex build-up to create the U-shape and pivot points in latex. Other disclosures in the prior art would require special machines to cast a glove with a pre-formed cuff, such as FIGS. 6 and 6A of the '945 patent, in order for the cuff to maintain its position relative to the glove.

It is an object of the present invention to provide an embodiment of a glove with a cuff.

It is an object of the present invention to provide an embodiment of a glove with a cuff, wherein the cuff has a relaxed position and a locked position.

It is another object of the present invention to provide an embodiment of a glove having an annular ridge.

It is still another object of the present invention to provide an embodiment of a glove having an annular ridge with a surface and V-shaped channels on both sides of the surface.

It is still another object of the present invention to provide an embodiment of a glove having creases on both sides of the annular ridge.

It is still another object of the present invention to provide an embodiment of a glove having V-shaped channels with bottom portions, the bottom portions having thickness less than the sleeve portion, rim portion, or cuff portion of the glove.

It is another object of the present invention to provide an embodiment of a glove having an abrupt transition at the fold of a cuff portion.

It is an object of the present invention to provide an embodiment of a glove with a cuff folded over either side of the annular ridge.

It is an object of the present invention to provide an embodiment of a glove with an annular ridge and an additional annular ridge.

It is another object of the present invention to provide an embodiment of a glove with either of two V-shaped channels to set the fold of the cuff portion.

It is an object of the present invention to provide an embodiment of a glove by a dipping process without flow disruption of the latex.

It is another object of the present invention to provide an embodiment of a glove by a dipping process with a groove and smooth flow.

These and other objectives and advantages of the present invention will become apparent from a reading of the attached specifications and appended claims.

SUMMARY OF THE INVENTION

Embodiments of the present invention include a glove with a hand portion, a sleeve portion, a cuff portion, and a connection portion. The sleeve portion is made integral to the hand portion and extends conically outward from the hand portion. The cuff portion 16 made integral with the sleeve portion and extends conically outward from the sleeve portion. The connection portion is set between the cuff portion and the sleeve portion, so that pivot of the fold is at the connection portion. In embodiments of the present invention, the connection portion comprises an annular ridge. The annular ridge has a surface, a first V-shaped channel on a first side of the surface, and a second V-shaped channel on a second side of the surface.

The annular ridge of the connection portion is a transition between the smooth sleeve portion and the cuff portion. The annular ridge has a partial cross-section formed by a first side wall, the surface, and a second side wall. The partial cross-section is generally rectangular with sharp edges formed at both ends of the surface. The first side wall is generally orthogonal to the surface, and the second side wall is generally orthogonal to the surface on an opposite side of the surface. The V-shaped channels form creases to define the pivot for the fold on either side of the surface so that there is no ambiguity or gradual thickening or poorly defined bulge to set the pivot. The V-shaped channels have reduced thickness at the bottom of the channel, which can also define the pivot for the fold on either side of the surface. The edges of the annular ridge are made integral and continuous with the adjacent portions. There is a cinching relationship as the smaller diameter of the annular ridge abruptly expands to the adjacent portion.

The V-shaped channels form the respective pivot points for different folds of the cuff portion over the sleeve portion. There is the first locked position with the first V-shaped channel collapsed so as to fold the cuff portion over the sleeve portion. The sleeve portion faces the surface to support the fold. There is also the second locked position with the second V-shaped channel collapsed so as to fold the cuff portion over the sleeve portion with the cuff portion facing the surface.

In other embodiments, the connection portion also has a rim portion and an additional annular ridge. The additional annular ridge has the same respective additional surface and additional V-shaped channels. The additional V-shaped channels have additional creases to define the pivot for another fold so that there is no ambiguity for this other fold. The additional V-shaped channels can also have respective additional bottom ends of the channels with thickness smaller than the sleeve portion, rim portion, or cuff portion. The bottom ends are also the pivot for the folds on either side of the additional surface. The additional V-shaped channels of the additional annular ridge can also form the fold with the pivot and support, similar to the annular ridge. Any one or combination of the four V-shaped channels can set the pivot for the fold and support by the respective surface of either annular ridge or additional annular ridge. The creases and cinching relationship of the additional creases and respective adjacent portions are also repeated.

Embodiments of the present invention also include the method of assembling the glove. A mold is formed with a hand section, a sleeve section made integral with the hand section, a cuff section, and a connection section between the sleeve section and the cuff section. The connection section has a groove between the sleeve section and the cuff section and with squared edges and an inset diameter smaller than the cuff section. The mold is dipped into a glove composition in liquid form, such as rubber or latex, from the hand section to the cuff section. Then, the mold is removed from the glove composition so as to allow excess glove composition to drip from the mold. The glove composition flows from the cuff section across the connection portion, across the sleeve section, and along the hand section so as to drip from the hand section. The glove composition fills the groove, and then flows smoothly over the groove from the cuff section to the sleeve section. The glove composition is cured on the mold so as to form a layer. The layer is removed from the mold by folding the layer inside out, the layer corresponding to the hand section forming the hand portion, the layer corresponding to the sleeve section forming the sleeve portion, the layer corresponding to the cuff section forming the cuff portion, the layer corresponding to the connection section forming the connection portion.

DETAILED DESCRIPTION OF THE DRAWINGS

Referring to FIGS. 1-6, embodiments of the present invention include a glove 10, 110, with a hand portion 12, 112, a sleeve portion 14, 114, a cuff portion 16, 116, and a connection portion 18, 118. The hand portion 12, 112 covers the fingers and palm of the wearer and has cavities for the five digits. The palm side can be textured, as well as the fingertips, for improved gripping action. The sleeve portion 14, 114 is made integral to the hand portion 12, 112 and extends conically outward from the hand portion 12, 112. The sleeve portion 14, 114 is generally frustoconical and covers the wrist and forearm of the wearer. The cuff portion 16, 116 is made integral with the sleeve portion 14, 114 and extends conically outward from the sleeve portion 14, 114. The cuff portion 16, 116 is the end of the glove 10, 110 with the opening for insertion of the hand of the wearer. The cuff portion 16, 116 flares out as the generally conical shape of the sleeve portion 14, 114 spreads and the cuff portion 16, 116 spreads. Prior art cuff portions can have textured outer surfaces and reinforced support to maintain integrity of the glove. The cuff portions can also have different colors than the sleeve and hand portions. The typical problem with the cuff portion is the inability to prevent liquid from dripping from the hand portion, along the sleeve portion, and pass the cuff portion to the arm of the wearer. Liquids, like water, run down the glove and wet the wearer. The present invention folds the cuff portion over the sleeve portion to form a barrier. Liquid will no longer be able to run down the glove and onto the wearer. The folded cuff portion prevents the liquid or water from contacting the wearer.

In embodiments of the present invention of FIGS. 1-6, there is a connection portion 18, 118 between the cuff portion 16, 116 and the sleeve portion 14, 114. The connection portion 18, 118 is the location or pivot of the fold so that the cuff portion 16, 116 inverts to be positioned over the sleeve portion 14, 114. Liquid will flow down the hand portion 14, 114 and the sleeve portion 16, 116 until turning at the connection portion 18, 118 to encounter the inverted cuff portion 16, 116, which stops flow from the arm of the wearer.

Figure 1:
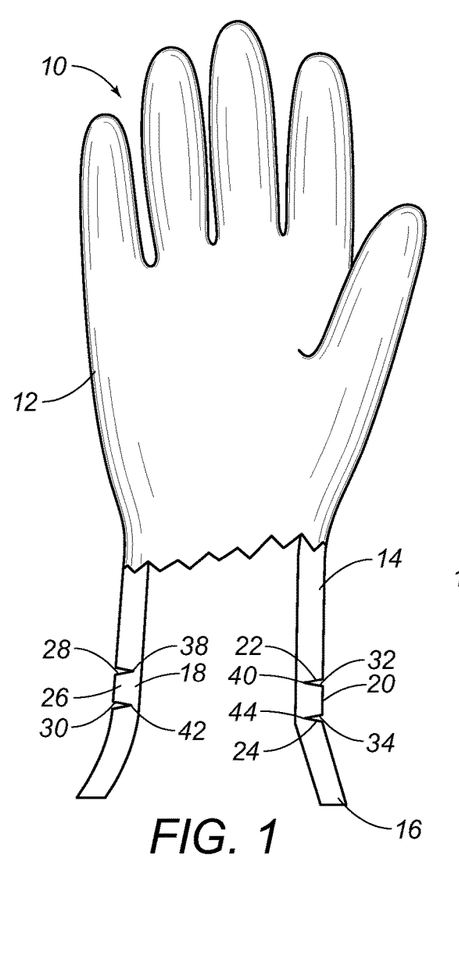
FIG. 1 is a schematic view of an embodiment of the glove with a cuff portion according to the present invention, showing the relaxed position.
Figure 3:
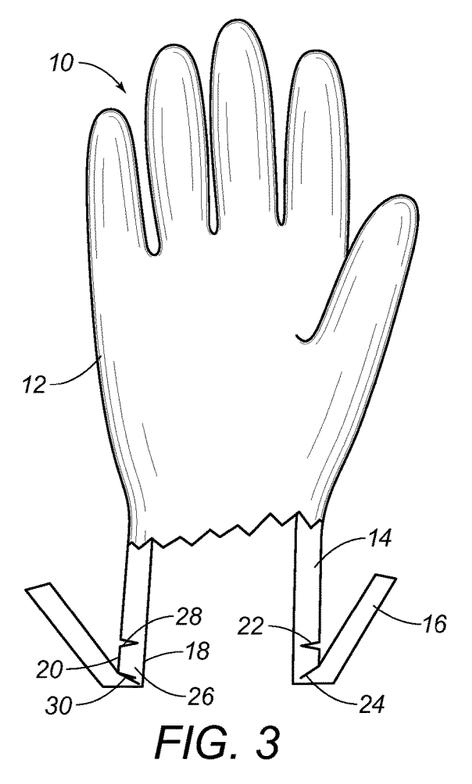
FIG. 3 is a schematic view of an embodiment of the glove with a cuff portion according to the present invention, showing a fold at the first V-shaped channel.
Figure 4:
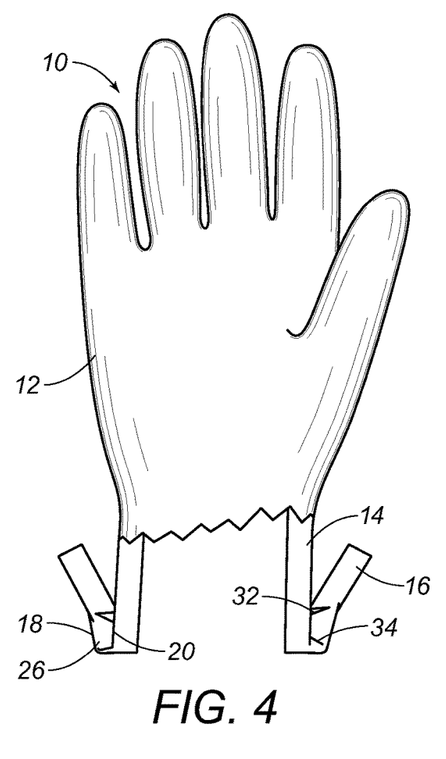
FIG. 4 is a schematic view of an embodiment of the glove with a cuff portion according to the present invention, showing a fold at the second V-shaped channel.

FIGS. 1, 3 and 4 show embodiments of the connection portion 18 with the glove 10 in the relaxed position, a first locked position, and a second locked position, respectively. In FIG. 1, the cuff portion 16 and the sleeve portion 14 are in alignment, and there is no barrier to liquid flow down the glove 10. The relaxed position facilitates putting on the glove 10 and taking off the glove 10. In FIGS. 1, 3 and 4, the connection portion 18 comprises an annular ridge 26. The annular ridge 26 has a surface 20, a first V-shaped channel 22 on a first side 28 of the surface 20, and a second V-shaped channel 24 on a second side 30 of the surface 20. In the relaxed position shown in FIG. 1, the surface 20 is generally parallel to the sleeve portion 14. The surface 20 can be flat. The thickness of the annular ridge 26 at the surface 20 can be the same as the thickness of the sleeve portion 14, the cuff portion 16 or both. The surface 20 can appear "raised" because the thickness is greater than the thickness of either of the V-shaped channels 22, 24. The surface 20 is not necessarily greater in thickness than either the sleeve portion 14, the cuff portion 16 or both.

The embodiments show the annular ridge 26 of the connection portion 18 as a transition between the smooth sleeve portion 14 and the smooth cuff portion 16. The annular ridge 26 defines the pivot of a fold without the ambiguity of the prior art curvatures and bulges. The strongly defined pivot allows the present invention to preset and support the fold with sharp edges and flat surfaces. The difficulty of casting the bulges or round beads and thinned walls is completely avoided by the present invention. FIGS. 1, 3 and 4 show the annular ridge 26 having a partial cross-section formed by a first side wall 32, the surface 20, and the second side wall 34. The partial cross-section can be generally rectangular with sharp edges formed at both the first side 28 and second side 30 of the surface 20. The first side wall 32 is generally orthogonal to the surface 20 and forms a sharp edge on the first side 28. The sharp edge can be a type of square edge. The second side wall 34 can also be generally orthogonal to the surface 20 on an opposite side, the second side 30, of the surface 20, forming another sharp edge.

In embodiments of the invention, the first V-shaped channel 22 forms a first crease 38 adjacent the sleeve portion 14, and the second V-shaped channel 24 forms a second crease 42 adjacent the cuff portion 16. The creases 38, 42 form the pivot for the cuff portion 16 to fold over the sleeve portion 14. The creases 38, 42 predetermine the location of the pivot. The creases 38, 42 are well defined pivots so there is no ambiguity about which portion of the glove 10 is best able to fold. The present invention pre-determines the possible folds. The creases 38, 42 are the most structurally obvious points for folding. The creases 38, 42 cinch the adjacent portion to the annular ridge 26. The first crease 38 is continuous with the adjacent sleeve portion 14 and clinches the sleeve portion 14 to the crease 38. The second crease 42 is continuous with the adjacent cuff portion 16 and cinches the cuff portion 16 to the annular ridge 26. The overall shape of the glove is conical, so the diameters are increases from the wrist of the hand portion 12 to the cuff portion 16. In the present invention, the first crease 38 has a first diameter smaller than the sleeve portion 14, and the second crease 42 has a second diameter smaller than the cuff portion 16. The smaller diameters cause the cinching relationship between the portions adjacent the connection portion 18.

In other embodiments, the first V-shaped channel 22 has a first bottom end 40 with a thickness less than the sleeve portion 14. The second V-shaped channel 24 can have a second bottom end 44 with a thickness less than the cuff portion 16. These bottom ends 40, 44 are located at the deepest point of the V-shape, respectively. These bottom ends 40, 44 are portions of the glove 10 with the smallest thickness, which also define the pivots for folding. The point with the smallest thickness can also define the pivot for the folds. The bottom ends 40, 44 form the pivot point analogous to the creases 38, 42. The smaller diameters of the bottom ends 40, 44 cinch the adjacent portion, forming a distinct pivot. Another alternative embodiment includes a plurality of pin holes (not shown) on the connection portion 18. In particular, the pin holes are placed in the bottom ends 40, 44 of the V-shaped channels 22, 24 or along the creases 38, 42. The pin holes weaken the layer of material so that the material is more flexible at the pivot. Pin holes further reinforce the set position of the fold without weakening an entire portion as in the prior art.

FIGS. 3-4 show the locked positions of the glove 10 with a cuff formed by the cuff portion 16. For the annular ridge 26, FIG. 3 shows the first locked position with the first V-shaped channel 22 collapsed so as to fold the cuff portion 16 over the sleeve portion 14. The sleeve portion 14 faces the surface 20. FIG. 4 shows the second locked position with the second V-shaped channel 24 collapsed so as to fold the cuff portion 16 over the sleeve portion 14 with the cuff portion 16 facing the surface 20. FIGS. 3 and 4 show an embodiment with one annular ridge 26. There are two distinct folds to hold the cuff portion 16 over the sleeve portion 14. Either fold can hold, so that the user is able to pull the cuff portion 16 to either locked position. Wear on the V-shaped channels 22, 24 can reduce strength of the locked position, so the remaining channel 22, 24 can still be an alternative to the worn channel. The present invention can have a longer working life as a glove with a locked cuff.

Figure 2:
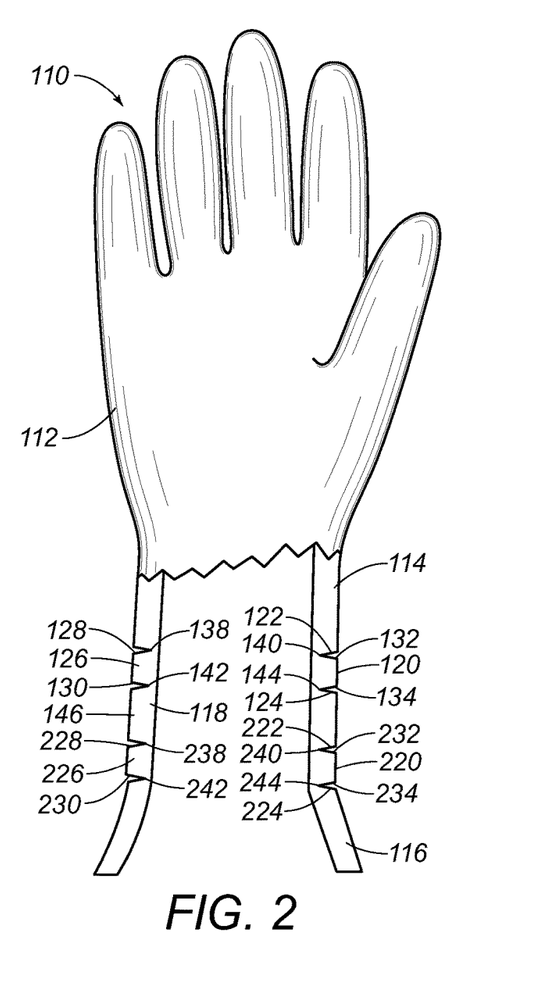
FIG. 2 is another schematic view of another embodiment of the glove with a cuff portion according to the present invention with the annular ridge, the rim portion and the additional annular ridge.
Figure 5:
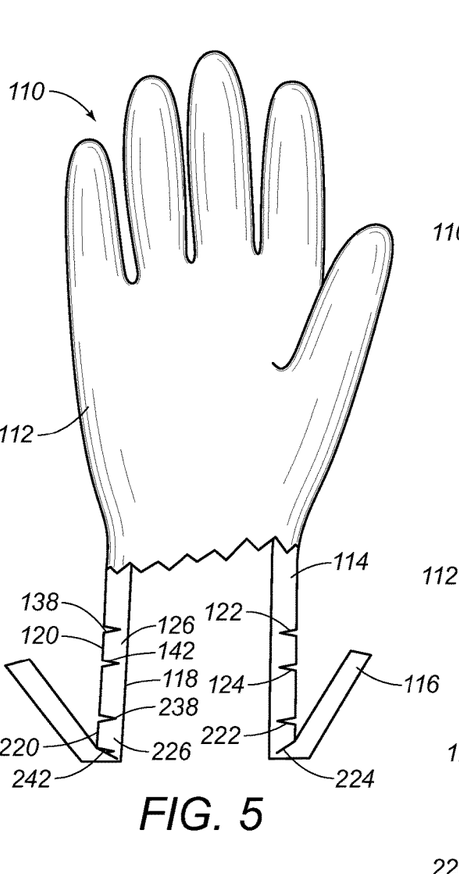
FIG. 5 is a schematic view of an alternative embodiment of the glove with a cuff portion according to the present invention, showing a fold at the additional first V-shaped channel.
Figure 6:
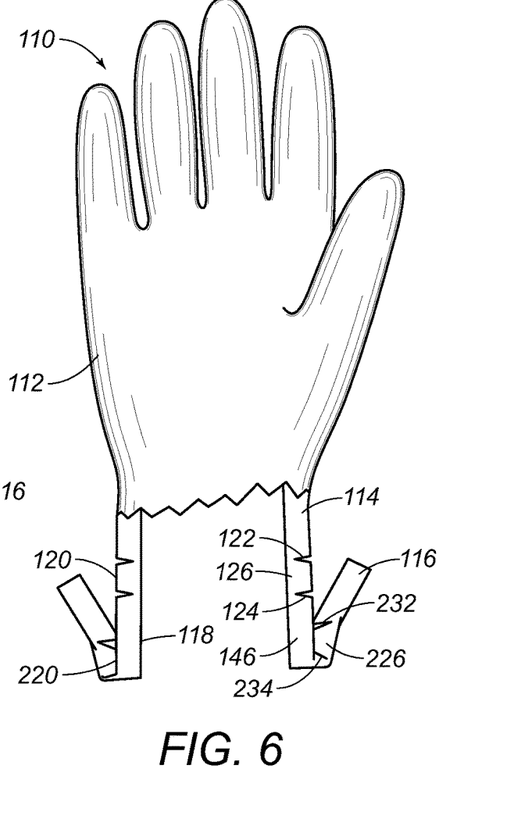
FIG. 6 is a schematic view of an alternative embodiment of the glove with a cuff portion according to the present invention, showing a fold at the additional second V-shaped channel.

An alternative embodiment of the glove 110 is shown in FIGS. 2, 5 and 6, which show the connection portion 118 with an annular ridge 126, a rim portion 146 and an additional annular ridge 226. The annular ridge 126 comprises a surface 120, a first V-shaped channel 122 on a first side 128 of the surface 120, and a second V-shaped channel 124 on a second side 130 of the surface 120. Structures of the annular ridge 126 are directly analogous to the annular ridge 26 of the embodiment of FIGS. 1, 3 and 4. The annular ridge 126 has a partial cross-section formed by a first side wall 132, the surface 120, and the second side wall 134. The partial cross-section can be generally rectangular with sharp edges formed at both the first side 128 and second side 130 of the surface 120 by the first side wall 132 and the second side wall 134 being generally orthogonal to the surface 120. Furthermore, the first V-shaped channel 122 forms a first crease 138 adjacent the sleeve portion 114. Now in the embodiments of FIGS. 2, 5 and 6, the second V-shaped channel 124 forms a second crease 142 adjacent the rim portion 146. Similarly, the first V-shaped channel 122 can have a first bottom end 140 with a thickness less than the sleeve portion 114, and the second V-shaped channel 124 can have a second bottom end 144 with a thickness less than the rim portion 146. Analogous folds at the V-shaped channels 122, 124 set the pivot of the cuff portion 116 over the sleeve portion 114.

Embodiments in FIGS. 2, 5 and 6 add the additional annular ridge 226. The additional annular ridge 226 comprises an additional surface 220, an additional first V-shaped channel 222 on an additional first side 228 of the additional surface 220, and an additional second V-shaped channel 224 on an additional second side 130 of the additional surface 220. Structures of the additional annular ridge 226 are directly analogous to the annular ridge 126. The additional annular ridge 226 has a partial cross-section formed by an additional first side wall 232, the additional surface 220, and the additional second side wall 234. The partial cross-section can be generally rectangular with sharp edges formed at both the additional first side 228 and additional second side 230 of the additional surface 220 by the additional first side wall 232 and the additional second side wall 234 being generally orthogonal to the additional surface 220.

Now in the embodiments of FIGS. 2, 5 and 6, the additional first V-shaped channel 222 forms an additional first crease 238 adjacent the rim portion 146, and the additional second V-shaped channel 224 forms an additional second crease 242 adjacent the cuff portion 116. Similarly, the additional first V-shaped channel 222 can have an additional first bottom end 240 with a thickness less than the sleeve portion 114, and the additional second V-shaped channel 224 can have an additional second bottom end 244 with a thickness less than the rim portion 146. Analogous folds at the additional V-shaped channels 222, 224 set the pivot of the cuff portion 116 over the sleeve portion 114. In this embodiment, all creases 138, 142, 238, 242 cinch the respective adjacent portions to the annular ridges 126, 226. The first crease 138 is continuous with the adjacent connection portion 118 and sleeve portion 114 and clinches the connection portion 118 to the crease 138. The second crease 142 is continuous with the adjacent cuff portion 116 and cinches the cuff portion 116 to the annular ridge 126. The additional first crease 238 and additional second crease 242 are continuous with the respective adjacent sleeve portion 114 to clinch the sleeve portion 114 to the crease 238 and continuous with the respective adjacent connection portion 118 to clinch the connection portion 118 to the annular ridge 226. The overall shape of the glove remains conical, so the diameters are increasing from the wrist of the hand portion 112 to the cuff portion 116. In the present invention, the first crease 138 has a first diameter smaller than the adjacent connection portion 118, the second crease 142 has a second diameter smaller than the cuff portion 116, the additional first crease 238 has an additional first diameter smaller than the adjacent sleeve portion 116, and the additional second crease 242 has an additional second diameter smaller than the connection portion 118. The smaller diameters cause the cinching relationship between the portions adjacent the connection portion 118.

In embodiments of the present invention, the rim portion 146 is generally frustoconical, extending from the annular ridge 126 and the sleeve portion 114 to the additional annular ridge 226 and the cuff portion 116. The rim portion 146 can have a thickness analogous to the sleeve portion 114, the cuff portion 116 or both. Variations may include the rim portion 146 having a different thickness, such as thinner or thicker than the sleeve portion 114. In the relaxed position shown in FIG. 2, the surface 120 and the additional surface 220 are generally parallel to the sleeve portion 114. The rim portion 146 extends conically outward from the annular ridge 126 to the additional annular ridge 226. The annular ridge 126 connects to the sleeve portion 114, and the additional annular ridge 226 connects to the cuff portion 116.

The creases 138, 142, 238, 242 are now all well defined pivots so there is no ambiguity about which portion of the glove 110 is best able to fold. The present invention predetermines the possible folds at these four options. The creases 138, 142, 238, 242 become the most structurally obvious points for folding. In other embodiments, the first bottom end 140, the second bottom end 144, the additional first bottom end 240, and the additional second bottom end 244 have thicknesses less than the respective sleeve portion 114, rim portion 146, or cuff portion 116. These bottom ends 140, 144, 240, 244 at the deepest point of the V-shape, respectively also define pivots for folding, as the smallest thicknesses of the glove 110. The V-shaped channels 122, 124, 222, and 224, form the respective pivot points for different folds of the cuff portion 116 over the sleeve portion 114. The channels 122, 124, 222, and 224, are formed by pre-cut slots in the mold of the glove 110. The flaring of the cuff portion 116 maintains the fold of the cuff portion 116.

FIGS. 5-6 show various embodiments of the additional locked positions of the glove 110 with a cuff formed by the cuff portion 116. For the annular ridge 126, the locked positions are not shown in FIGS. 5 and 6. These locked positions are directly analogous to FIGS. 3 and 4 with folds on both sides of annular ridge 26. Folds at annular ridge 126 are possible in the embodiments of FIGS. 5 and 6, but not shown.

For the annular ridge 226, FIG. 5 shows the additional first locked position with the first V-shaped channel 222 collapsed so as to fold the cuff portion 116 over the rim portion 146 and sleeve portion 114. The rim portion 146 faces the additional surface 220. FIG. 6 shows the additional second locked position with the second V-shaped channel 224 collapsed so as to fold the cuff portion 116 over the rim portion 146 and the sleeve portion 114 with the cuff portion 116 facing the additional surface 220. FIGS. 5 and 6 show an embodiment with one annular ridge 126 and an additional annular ridge 226. There are four distinct folds to hold the cuff portion 116 over the sleeve portion 114. The user is able to pull the cuff portion 116 to any of four locked positions. Wear on channels 122, 124, 222, 224 is further distributed across four pivots for an even longer working life as a glove with a locked cuff.

Embodiments of the present invention include the method of assembling the glove. The method includes forming a mold with a hand section, a sleeve section made integral with the hand section, a cuff section, and a connection section between the sleeve section and the cuff section. The method also includes dipping the mold into a glove composition in liquid form from the hand section to the cuff section and then removing the mold from the glove composition so as to allow excess glove composition to drip from the mold. The glove composition can be rubber or latex or similar material composition. The glove composition flows from the cuff section across the connection portion, across the sleeve section, and along the hand section so as to drip from the hand section. After dripping has stopped, the glove composition is cured on the mold so as to form a layer. Then, the layer is removed from the mold by folding the layer inside out, the layer corresponding to the hand section forming the hand portion, the layer corresponding to the sleeve section forming the sleeve portion, the layer corresponding to the cuff section forming the cuff portion, the layer corresponding to the connection section forming the connection portion.

In some embodiments, the connection section is comprised of a groove between the sleeve section and the cuff section, the groove having squared edges and an inset diameter smaller than the cuff section, at least one squared edge being made integral with the cuff section. The glove composition fills the groove and flows over the groove from the cuff section to the sleeve section after the groove is filled. The layer corresponding to the groove forms the annular ridge having the surface with the first V-shaped channel on the first side and the second V-shaped channel on the second side, the squared edges corresponding to the V-shaped channels. The annular ridge has a partial cross-section formed by a first side wall, the surface, and a second side wall. The partial cross-section is generally rectangular, corresponding to the shape of the groove on the mold. In particular, the surface can correspond to the layer on the inset diameter of the groove. The creases correspond to the layer on the squared edges of the groove. The creases cinching the connection portion. The first crease has a first diameter smaller than the connection portion, and the second crease has a second diameter smaller than the cuff portion. In the present invention, the first crease remains continuous and integral with the connection portion, and the second crease remains continuous and integral with the cuff portion.

The method also includes forming a glove with the connection section further comprised of an additional groove between the sleeve section and the cuff section. The additional groove has additional squared edges and an additional inset diameter smaller than the sleeve section, at least one additional squared edge being made integral with the sleeve section. The additional groove is adjacent the sleeve portion, and the groove is adjacent the cuff portion. The additional groove and the groove are placed on opposite sides of the connection portion. The dipping, the dripping and flowing are all in line with the sequence of the hand section, sleeve section, additional groove, groove, and the cuff section. The additional groove is similarly filled and flowed over in this order relative to the other parts of the mold. The additional V-shaped channels and creases enable additional cinching at the additional locations at the additional channels and creases. The additional locking positions on the glove are now formed with the connection section with more than one groove.

Embodiments of the present invention provide a glove with a cuff. There is a relaxed position to facilitate wearing the glove and removing the glove. There are different embodiments of locked positions of the glove, wherein the cuff portion is folded over the sleeve portion to form a barrier at the connection portion. Depending upon how much and how hard the user pulls the cuff portion, a different locked position can be engaged. Each locked position sets a cuff by the cuff portion. There can be variations in size of the cuff, depending on how much cuff portion is pulled. The barrier prevents liquid from leaking onto the wearer from the hand portion and sleeve portion of the glove.

In the present invention, the connection portion has an annular ridge with a surface and V-shaped channels on both sides of the surface. The sides of the annular ridge cut into the glove to set a pivot of the fold of the glove. In some embodiments, there are creases formed by the V-shaped channels. In other embodiments, the bottom end of each V-shaped channel sets a pivot for the fold. Either side of the annular ridge can set the pivot at V-shaped channels. There is no thickening or bead to set the pivot. There is also no thinned wall between beads. Less material is used, and the embodiments of the present invention direct the pivot towards folding over the sleeve portion only. The round beads or thickened bulges of the prior art cannot achieve the directed and supported fold of the embodiments of the present invention.

The annular ridge of the connection portion forms an abrupt transition between the smooth sleeve portion and the smooth cuff portion. The pivot of a fold is set without the ambiguity of the prior art curvatures and bulges. The pivot can be set on either side of the annular ridge. Additionally, pivots can be set by either the annular ridge or the additional annular ridge, when there are two ridges. The strongly defined pivot allows the present invention to set and support the fold with creases and flat surfaces. The annular ridge can have squared edges defined by the partial cross-section of the first side wall, surface, and the second side wall. The orthogonal relationship between the sides and surface form the predetermined pivot for the sleeve portion or the rim portion relative to the rim portion or cuff portion, respectively. The difficulty of casting the bulges, uneven thickening, and round beads is completely avoided by the present invention.

Other embodiments include connection portion with the annular ridge, the rim portion and an additional annular ridge. The additional annular ridge has the same additional surface and additional V-shaped channels for even more possible pivots. Any user of any size hands and arms can pull the desired amount of cuff portion to lock the cuff portion in place. The options for setting and supporting the fold of the cuff portion give flexibility in size and reduce wear on any one V-shaped channel. The working life of cuff, and the overall working life of the glove are extended by the embodiments of the present invention.

The foregoing disclosure and description of the invention is illustrative and explanatory thereof. Various changes in the details of the illustrated structures, construction and method can be made without departing from the true spirit of the invention.

I claim:

1. A glove, comprising:
   a hand portion;
   a sleeve portion being made integral to said hand portion and extending conically outward from said hand portion;
   a cuff portion being made integral with said sleeve portion and extending conically outward from said sleeve portion; and
   a connection portion between said cuff portion and said sleeve portion, said connection portion being comprised of an annular ridge on an exterior side of said connection portion, said cuff portion folding over said sleeve portion at said connection portion,
   wherein said annular ridge is comprised of a surface with a first V-shaped channel on a first side of said surface and a second V-shaped channel on a second side of said surface.

2. The glove according to claim 1, wherein said annular ridge has a partial cross-section formed by a first side wall, said surface, and a second side wall, said partial cross-section being generally rectangular.

3. The glove according to claim 2, wherein said first side wall is generally orthogonal to said surface, and wherein said second side wall is generally orthogonal to said surface on an opposite side of said surface.

4. The glove according to claim 1, wherein said first side wall forms a first crease adjacent said sleeve portion so as to cinch said connection portion to said first crease.

5. The glove according to claim 4, wherein said second side wall forms a second crease adjacent said cuff portion so as to cinch said cuff portion to said second crease, and
   wherein said first crease has a first diameter smaller than said connection portion, said second crease having a second diameter smaller than said cuff portion, said first crease being continuous with said connection portion, said second crease being continuous with said cuff portion.

6. The glove according to claim 1, wherein said first V-shaped channel has a first bottom end with thickness less than said sleeve portion.

7. The glove according to claim 6, wherein said second V-shaped channel has a second bottom end with thickness less than said cuff portion.

8. The glove according to claim 1, wherein said connection portion is comprised of a plurality of pin holes, said pin holes being covered by said cuff portion when said cuff portion folds over said sleeve portion.

9. The glove according to claim 1, wherein said cuff portion has a relaxed position with said surface generally parallel to the sleeve portion,
wherein said cuff portion has a first locked position with the first V-shaped channel collapsed, said cuff portion folding over said sleeve portion, said sleeve portion facing said surface, and
wherein said cuff portion has a second locked position with the second V-shaped channel collapsed, said cuff portion folding over said sleeve portion, said cuff portion facing said surface.

10. The glove according to claim 1, wherein said connection portion further comprises:
an additional annular ridge; and
rim portion between said annular ridge and said additional annular ridge, said rim portion extending conically outward from said annular ridge to said additional annular ridge,
wherein said annular ridge connects to said sleeve portion, wherein said additional annular ridge connects to said cuff portion, and
wherein said additional annular ridge has an additional surface, an additional first V-shaped channel on an additional first side of said additional surface, and an additional second V-shaped channel on an additional second side of said additional surface.

11. The glove according to claim 10, wherein said annular ridge has a partial cross-section formed by a first side wall, said surface, and a second side wall, said partial cross-section being generally rectangular, and
wherein said additional annular ridge has a partial cross-section formed by said additional first side wall, said additional surface, and said additional second side, said partial cross-section being generally rectangular.

12. The glove according to claim 11, wherein said first side wall is generally orthogonal to said surface,
wherein said second side wall is generally orthogonal to said surface on an opposite side of said surface,
wherein said additional first side wall is generally orthogonal to said additional surface, and
wherein said additional second side wall is generally orthogonal to said additional surface on an opposite side of said additional surface.

13. The glove according to claim 10, wherein said first side wall forms a first crease adjacent said sleeve portion so as to cinch said connection portion to said first crease, wherein said second side wall forms a second crease adjacent said rim portion so as to cinch said rim portion to said second crease, wherein said additional first side wall forms a first additional crease adjacent said rim portion so as to cinch said connection portion to said first additional crease, wherein said additional second side wall forms a second additional crease adjacent said cuff portion so as to cinch said cuff portion to said second crease,
wherein said first crease has a first diameter smaller than said connection portion, said first crease being continuous with said connection portion,
wherein said second crease has a second diameter smaller than said rim portion, said second crease being continuous with said rim portion,
wherein said additional first crease has a first additional diameter smaller than said rim portion, said additional first crease being continuous with said rim portion, and
wherein said additional second crease has a second additional diameter smaller than said cuff portion, said additional second crease being continuous with said cuff portion.

14. The glove according to claim 10, wherein said first V-shaped channel has a first bottom end with thickness less than said sleeve portion, wherein said second V-shaped channel has a second bottom end with thickness less than said rim portion, wherein said first additional V-shaped channel has a first additional bottom end with thickness less than said rim portion, and wherein said second additional V-shaped channel has a second additional bottom end with thickness less than said cuff portion.

15. The glove according to claim 10, wherein said cuff portion has a relaxed position with said surface and said additional surface generally parallel to said sleeve portion,
wherein said cuff portion has a first locked position with the first V-shaped channel collapsed, said cuff portion and said rim portion folding over said sleeve portion, said sleeve portion facing said surface,
wherein said cuff portion has a second locked position with the second V-shaped channel collapsed, said cuff portion and said rim portion folding over said sleeve portion, said rim portion facing said surface,
wherein said cuff portion has a third locked position with the additional first V-shaped channel collapsed, said cuff portion folding over said rim portion and said sleeve portion, said rim portion facing the additional flat surface, and
wherein said cuff portion has a fourth locked position with the additional second V-shaped channel collapsed, said cuff portion folding over said rim portion and said sleeve portion, said cuff portion facing said additional flat surface.

16. A method of assembling the glove according to claim 1, said method comprising the steps of:
forming a mold with a hand section, a sleeve section made integral with said hand section, a cuff section, and a connection section between said sleeve section and said cuff section, said connection section being comprised of a groove between said sleeve section and said cuff section, said groove having squared edges and an inset diameter smaller than said cuff section, at least one squared edge being made integral with said cuff section;
dipping said mold into a glove composition in liquid form from said hand section to said cuff section;
removing said mold from said glove composition so as to allow excess glove composition to drip from said mold;
flowing glove composition from said cuff section across said connection portion, across said sleeve section, and along said hand section so as to drip from said hand section, wherein said glove composition fills said groove, and wherein said glove composition flows over said groove from said cuff section to said sleeve section after said groove is filled;

curing said glove composition on said mold after dripping has stopped so as to form a layer; and removing said layer from said mold by folding said layer inside out, said layer corresponding to said hand section forming said hand portion, said layer corresponding to said sleeve section forming said sleeve portion, said layer corresponding to said cuff section forming said cuff portion, said layer corresponding to said connection section forming said connection portion, wherein said layer corresponding to said groove forms said annular ridge on an exterior side of said connection portion having said surface with said first V-shaped channel on said first side of said surface and said second V-shaped channel on said second side of said surface, said squared edges corresponding to the V-shaped channels.

17. The method of assembling the glove according to claim 16, wherein said annular ridge has a partial cross-section formed by a first side wall, said surface, and a second side wall, said partial cross-section being generally rectangular, said surface corresponding to said layer on said inset diameter of said groove.

18. The method of assembling the glove according to claim 16, further comprising the steps of:

cinching said connection portion to a first crease, said first side wall forming said first crease adjacent said sleeve portion; and cinching said cuff portion to a second crease, said second side wall forming said second crease adjacent said cuff portion, wherein said first crease has a first diameter smaller than said connection portion, said second crease having a second diameter smaller than said cuff portion, said first crease being continuous with said connection portion, said second crease being continuous with said cuff portion.

19. The method of assembling the glove according to claim 16, wherein said connection section is further comprised of an additional groove between said sleeve section and said cuff section, said additional groove having additional squared edges and an additional inset diameter smaller than said sleeve section, at least one additional squared edge being made integral with said sleeve section, wherein the step of dipping said mold into a glove composition in liquid form from said hand section to said cuff section comprises dipping from said sleeve section to said additional groove of said connection section to said groove of said connection section and to said cuff section, wherein the step of flowing glove composition is further comprised of flowing from said cuff section across said groove of said connection portion, across said additional groove of said connection portion, along said sleeve section, and along said hand section so as to drip from said hand section, and wherein glove composition fills said groove and said additional groove, and wherein said glove composition flows over said groove and said additional groove from said cuff section to said sleeve section after said groove and said additional groove are filled.

20. The method of assembling the glove according to claim 19, wherein said layer corresponding to said additional groove forms an additional annular ridge having an additional surface with an additional first V-shaped channel on an additional first side and an additional second V-shaped channel on an additional second side, said additional squared edges corresponding to the additional V-shaped channels.

* * * * *